(12) United States Patent
Tsai et al.

(10) Patent No.: US 7,806,838 B2
(45) Date of Patent: Oct. 5, 2010

(54) IMAGE ANALYSIS METHOD FOR ABNORMAL HIP STRUCTURES BASED ON TRANSVERSE SECTIONS

(75) Inventors: Ming-Dar Tsai, Jhongli (TW); Ming-Shium Hsieh, Taipei (TW)

(73) Assignee: Chung Yuan Christian University, Taipei (TW)

( * ) Notice: Subject to any disclaimer, the term of this patent is extended or adjusted under 35 U.S.C. 154(b) by 1165 days.

(21) Appl. No.: 11/140,326

(22) Filed: May 27, 2005

(65) Prior Publication Data
US 2006/0111628 A1    May 25, 2006

(30) Foreign Application Priority Data
Nov. 23, 2004    (TW) .............................. 93135953 A

(51) Int. Cl.
*A61B 5/103* (2006.01)
(52) U.S. Cl. ...................................... 600/587; 382/128
(58) Field of Classification Search ................. 600/587; 382/128
See application file for complete search history.

(56) References Cited

U.S. PATENT DOCUMENTS 6,160,866 A * 12/2000 Mazess et al. ................. 378/56

OTHER PUBLICATIONS

Hsieh et al. "Automatic Spinal Fracture and Diagnosis and Surgical Management Based on 3D Image Analysis and Reconstruction of CT Transverse Sections" Oct. 2002.Biomedical Engineering -Applications, Basis and Communications, pp. 22-30.*

Tsai et al. "Automatic spinal disease diagnosis assisted by 3D unaligned transverse CT slices" May 3, 2004. Computerized Medical Imaging and Graphics. pp. 307-315.*

Nlreg "Spherical Regression—Fit a Sphere to Data Points" Dec. 20, 2003. http://web.archive.org/web/20031220210928/http://www.nlreg.com/sphere.htm.*

* cited by examiner

*Primary Examiner*—Max Hindenburg
*Assistant Examiner*—Renee Danega
(74) *Attorney, Agent, or Firm*—Thomas, Kayden, Horstemeyer & Risley

(57) ABSTRACT

An image analysis method for abnormal hip structures. A plurality of transverse sections of a bone structure are provided. Structural features on the transverse sections are obtained. Abnormalities of the structural features of the bone structure are recognized. Structural and feature properties of the bone structure are estimated according to recognition results, and corresponding structural parameters relating to the bond structure are obtained accordingly.

13 Claims, 17 Drawing Sheets
(9 of 17 Drawing Sheet(s) Filed in Color)

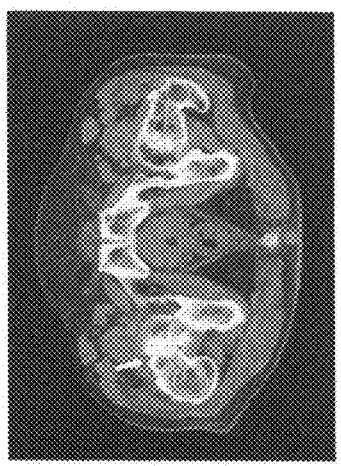
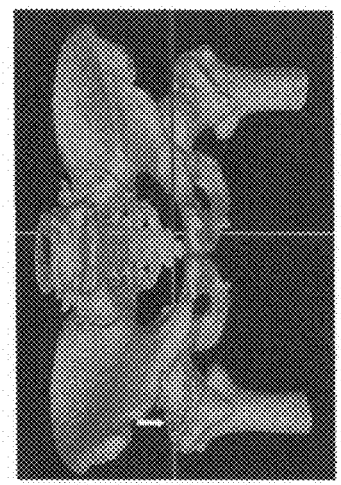
FIG. 13C
FIG. 13B
FIG. 13A

IMAGE ANALYSIS METHOD FOR ABNORMAL HIP STRUCTURES BASED ON TRANSVERSE SECTIONS

BACKGROUND

The present invention relates to image analysis methods, and more particularly, to image analysis methods for abnormal hip structures based on transverse sections.

Current modalities for hip surgery include preoperative evaluation using x-ray and intra-operative procedure determination using guide tools and template prostheses. The preoperative x-ray evaluation identifies abnormalities in hip structure and whether conservative, screw-plate or arthroplasty are suitable, and roughly determines the size of required screws, plates, and prosthetic components. The guide tools determine precise anatomical axes, cut bones to generate interfaces between bones and prosthetic components, and positioning of screws, nails, and plates. Template prostheses determine suitable prosthetic components. Relatively acceptable surgical procedures and prosthetic components can be obtained and hip function improved postoperatively using manual x-ray evaluation and trial-and-error methods with guide tools and template prostheses.

To achieve optimal hip function, surgeons the largest workable prosthesis to reduce average loading on the new joint or screws, nails, and plates, and define interfaces between bones and the prosthetic components, facilitating recovery of anatomical morphology of the hip. Additionally, procedures preferably aid selection of sections for interfaces and bones and prosthesis, positions for screws, nails and plates, and prosthetic components, thereby saving operation time. However, preoperative evaluation can be insufficient, such that avoiding uncertainty and overcoming difficulty during operation only by time-consuming trial and error, intraoperatively. Moreover, symmetry between hips and comfortable angles and distances among anatomical hip cannot be predicted using conventional trial-and-error based methods without evaluation of hip morphology.

Optimal attitude and positioning of prosthetic components are chosen for satisfactory bone morphology by evaluating X-ray cephalograms. However, image analyses, such as identifying landmarks and reference lines on the bone morphology, using X-ray projections, are limited by projection and dimension-reduction errors. An X-ray projection represents a three-dimensional (3D) structure two-dimensionally, transforming the centerline curve as a line, a 3D location, or section plan lines, and a 3D attitude as 2D angle, resulting in inaccurate management and surgical planning.

Thus, an improved image analysis method for abnormal hip structures based on transverse sections is desirable.

SUMMARY

Image analysis methods for abnormal hip structures are provided. In an embodiment of such a method, a plurality of transverse sections of a bone structure are provided. Structural features on the transverse sections are obtained. Abnormities in structural bone features are recognized. Structural and feature properties of the bone structure are estimated according to recognition results and corresponding structural parameters relating to the bond structure are obtained accordingly.

The image analysis method comprises approximating a stem canal, femur head, or acetabulum on transverse sections as elliptical structures using a B-spline function, or a femur neck as a cylindrical structure and a pelvis horizontally as symmetrical structures using a least square method.

According to the image analysis method, bone structure recognition further comprises determining an initial center of each stem canal on the transverse sections by averaging pixel positions of the bone structure or extrapolating the positions according to stem canal centers on inferior sections, intersecting a first bone boundary using a vector from the initial center along each integral angular position, interpolating a normal radius corresponding to each angular position inside a concave feature using radii of both ends of the concave feature of the stem canal, intersecting all bone boundaries using a vector from the stem canal centers along each integral angular position, and determining an axis regressed from the stem canal centers on the transverse sections.

The image analysis method for bone structure recognition further comprises determining a center of a femur stem by extrapolating a femur stem axis, intersecting a first bone boundary with a vector from the initial center along each integral angular position, interpolating a normal radius inside a concave or convex feature using radii of both ends of the structural feature, determining an initial centerline of the femur neck, regressing a new centerline according to midpoints of each pixel on the initial centerline, detecting tumors and fractures at the femur neck using surface normal lines at each pixel of the regressed centerline, determining a center plane of the femur neck according to centerlines on the transverse sections resolving the femur neck, orthogonally projecting the centerline of each transverse section onto the center plane of the femur neck to re-determine a centerline of the transverse sections and structural features of the femur neck, and determining a femur neck axis according to the re-determined centerline and structural features.

The image analysis method for bone structure recognition further comprises excluding a femur neck to obtain a femur head, intersecting boundaries of a femur head using a vector from an outmost point along each integral angular position to obtain multiple boundary intersections, averaging the boundary intersections to define an initial center of the head, determining structural features and normal radii to the boundaries of the femur head and the acetabulum using a vector from the initial center along each integral angular position, re-determining a center of the femur head and structural features according to the normal radii of the femur head, and regressing an axis of the femur head using centers on the transverse sections.

The image analysis method for bone structure recognition further comprises determining a middle point of the pelvis by averaging bone pixels thereof along each horizontal line of the transverse sections, regressing centerlines of the pelvis from the middle points, and determining a center plane according to the centerlines of the transverse sections.

A detailed description is given in the following embodiments with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention can be more fully understood by reading the subsequent detailed description and examples of embodiments thereof with reference made to the accompanying drawings, wherein:

FIG. 13A is a schematic of a 3D image revealing a fracture on the right femur neck;

FIG. 13B is a schematic of a transverse section for the right femur neck, as well as an analysis result indicating a large fracture at the right neck;

FIG. 13C is a schematic of another section for the left femur neck;

DETAILED DESCRIPTION

The invention discloses an image analysis method for abnormal hip structures based on transverse sections.

Figure 1:
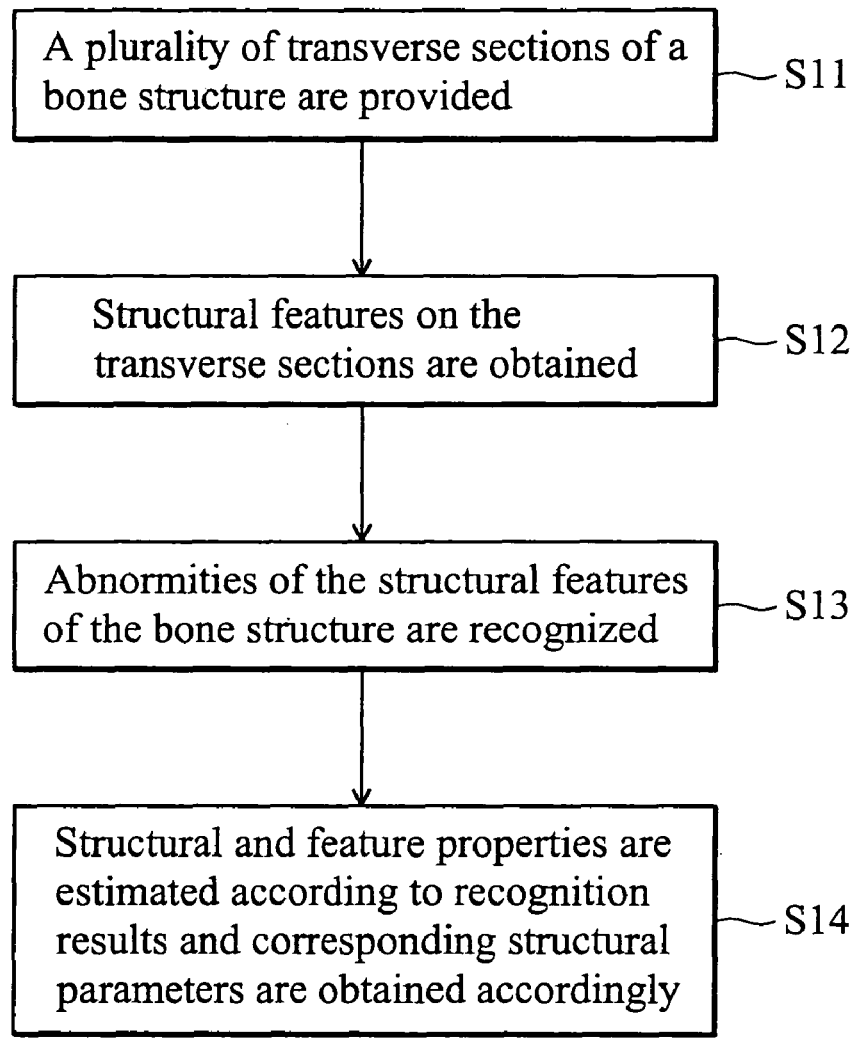
FIG. 1 is a schematic view of an embodiment of an image analysis method for abnormal hip structures based on transverse sections.

FIG. 1 is a schematic view of an embodiment of an image analysis method for abnormal hip structures based on transverse sections.

Hip structures, including acetabulum and femur stem, trochanter, neck and head, are first identified (step S11). Concave, convex and, perforated features on the hip structures are recognized (step S12). The features indicate abnormalities such as spur, fracture, and tumor respectively. Structural and feature properties, such as femur head radius, neck and stem axes, pelvis center plane, tumor and fracture positions, and deviated angles and dislocations among the hip structures are calculated (step S13). Tumor dissection and bone grafts are executed according to calculation results, recovering distances and angles of the hip structures. Additionally, the procedures can be simulated for verification and rehearsal using an orthopedic surgical simulator.

Figure 2A:
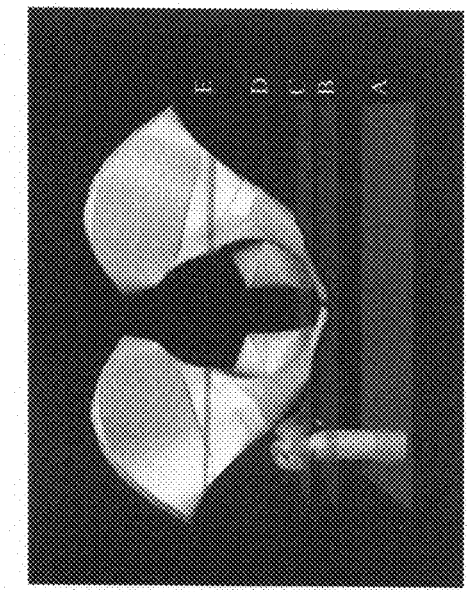
FIG. 2A is a schematic diagram of an idealized hip with neighboring anatomical structures including femur stem, trochanters, neck and head, acetabulum and pelvis.
Figure 2B:
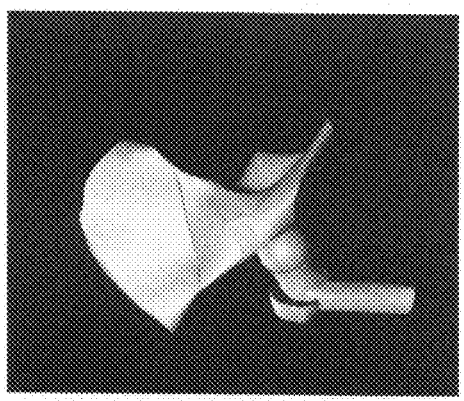
FIG. 2B is a schematic diagram of a femur with dislocation between a femur head and acetabulum.
Figure 2C:
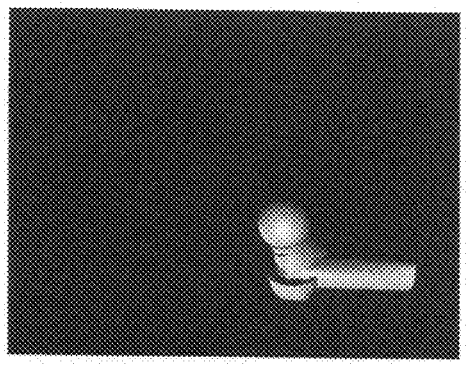
FIG. 2C is a schematic diagram of a fractured femur neck with angular deviations between a femur stem and neck axes.

FIG. 2A is a schematic diagram of an idealized hip with neighboring anatomical structures including femur stem, trochanters, neck and head, acetabulum and pelvis, with ratios of sizes of the structures and distances and angles thereof in normal ranges to maintain hip function. However, some conditions may change angles or distances, resulting in abnormalities in hip function, leading to further malady. A dislocated femur, for example, as shown in FIG. 2B, results in a displacement and angular deviation between the femur head and acetabulum, and a fracture on femur neck, as shown in FIG. 2C, results in an angular deviation between the femur stem and neck.

Figure 12A:
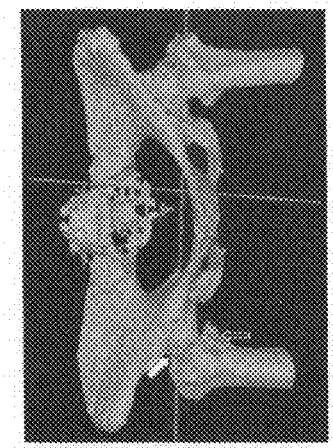
FIG. 12A is a schematic diagram of 3D reconstruction of a bone surface.
Figure 12B:
FIG. 12B is a schematic diagram of image analysis results on transverse sections for stems.
Figure 12C:
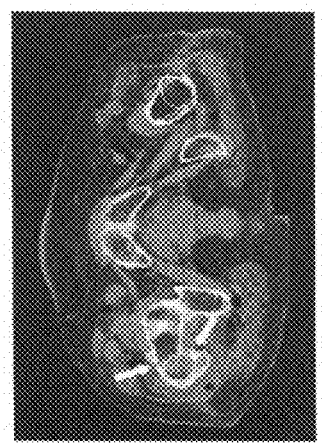
FIG. 12C is a schematic diagram of image analysis results on transverse section for trochanter fracture and neck compression.

A CT or Magnetic Resonance Imaging (MRI) transverse section may resolve the pelvis, acetabulum, with the femur head, neck and stem in separate areas of the section. A most inferior section, Section A shown in FIG. 2A, such as the section shown in FIG. 12B, resolves only two femur stems. A superior section, Section B shown in FIG. 2A, such as the section shown in FIG. 12C, resolves the stem associated with the lesser or greater trochanter or the femur neck, Section C in FIG. 2A, such as the section shown in FIG. 13B. The femur head and acetabulum are resolved with a further superior section, Section D in FIG. 2A, such as the section shown in FIG. 10B. The most superior section resolves only the pelvis, Section E shown in FIG. 2A).

With automatic detection of bone morphology including the described ratios (normal or abnormal), distances, and angles, recognition of hip structures and associated features is required. Recognition of morphologic structures and features is easily implemented using traditional (boundary representation or constructive solid geometry) solid models. For example, a convex or concave feature is recognized based on intersection computation results between original boundary edges and the lines connecting vertices. However, due to the lack of information related to geometric elements such as faces, edges, and vertices in volume data, structures and features cannot be easily recognized using the intersection computation. Tsai and Hsieh approximate 2D elliptical anatomical structures (disc spaces and vertebral bodies) with concave and convex features from transverse sections at the spine. The convex features at disc spaces are matched into a disc herniation feature and to for diagnose Herniated InterVertebral Disk (HIVD). The concave features at vertebral bodies are matched into a canal feature and used for diagnose canal compression. Tsai and Hsieh also combine 2D disc herniation features or centers of 2D vertebral bodies on respective multiple transverse sections to reconstruct 3D disc herniation or spinal curve to diagnose spinal deformities such as kyphosis and scoliosis.

The method of the invention analyzes bone morphology on transverse sections to detect whether the described ratios, distances, and angles are normal or abnormal to automate the diagnoses. On transverse sections at the hips, the acetabula are domed, the femur heads and stems are circular, and the femur necks are conical. In the invention, the described structures are first recognized at each transverse section. Concave, convex, and perforated features associated with the structure are then recognized. The features can reveal other structures such as trochanters (from the femur stem), or deformities such as fractures, spurs, and tumors. Some properties from multiple transverse sections, such as centers of the stem canal, femur head, and acetabulum, can calculate centers of acetabulum and the femur head, and axes of acetabulum and the femur head, neck, and stem. The 2D features can be also combined to calculate the volumes of fractures or tumors.

Properties of abnormal structures define required surgery as dissection and grafting, open reduction, or hemi- or total-arthroplasty. Next, accurate procedures are planned, including positions for dissection of tumors and bone grafts, the attitude of prosthetic components and nail-plate-screws, displacements and deviated angles for recovery, and sizes of bone graft and prosthetic components.

Anatomical structure and feature recognition are described as follows.

An image process system of the invention processes transverse sections along an anti-gravity direction. A femur neck appears together with the stem and trochanters in superior sections. Femur stem exclusion enables recognition of trochanters and the femur neck. Next, a method for acetabulum and the femur head comprises femur head possibly appearing together with the femur neck in a superior section.

Figure 3:
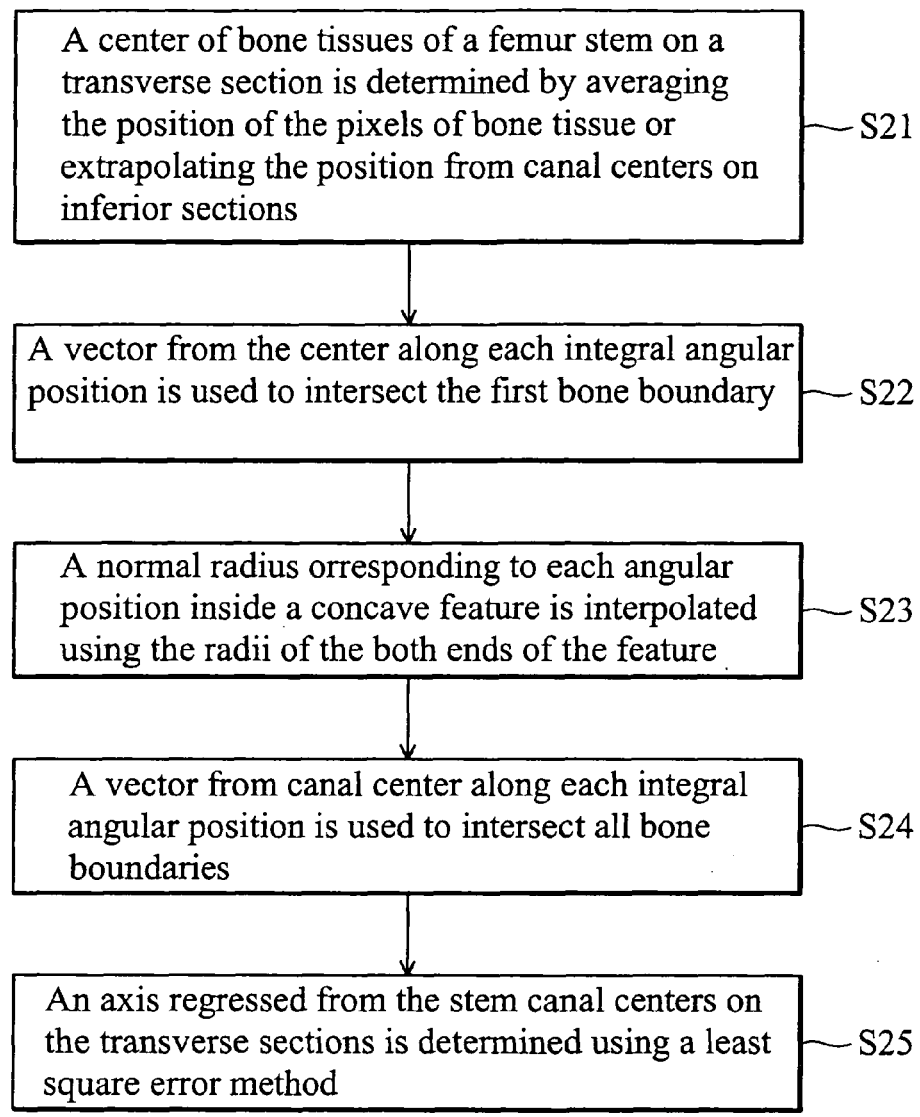
FIG. 3 is a flowchart of an embodiment of a method for femur stem recognition on transverse sections.

FIG. 3 is a flowchart of an embodiment of a method for femur stem recognition on transverse sections.

Figure 4C:
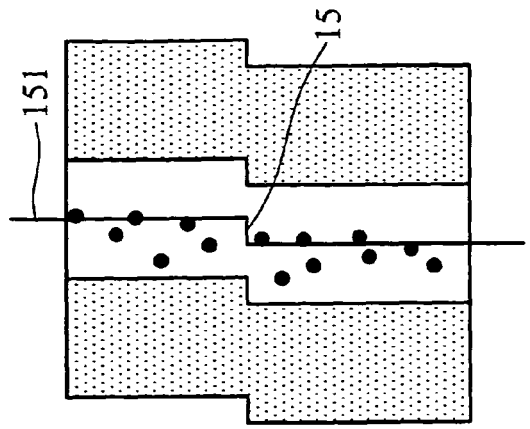
FIG. 4C is a schematic diagram of shear displacement by two centerlines regressed from two separate groups of 2D canal centers.
Figure 4B:
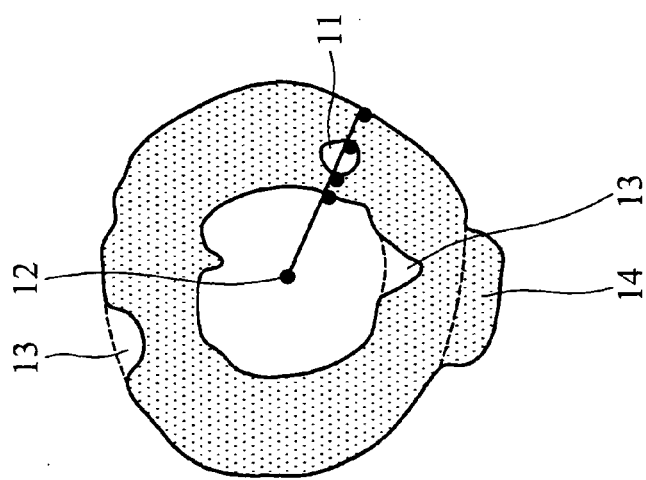
FIG. 4B is a schematic diagram of a center of B-spline approximate canal boundary and convex and concave features on an outside bone boundary.
Figure 4A:
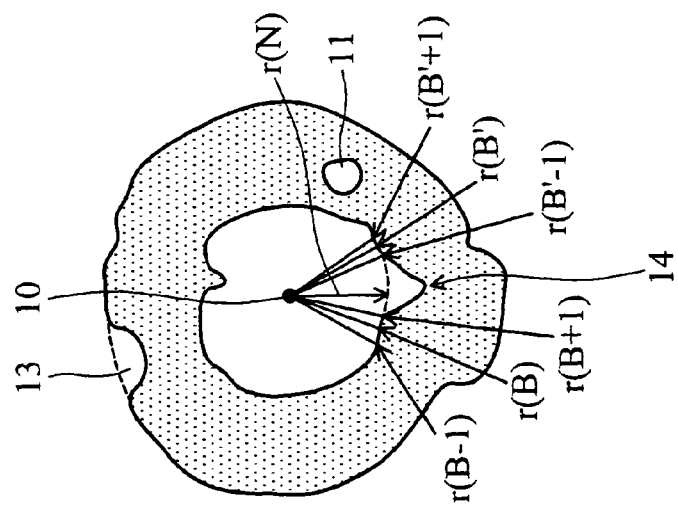
FIG. 4A is a schematic diagram of an initial center of stem canal and convex and concave features on canal boundary.

A center 10 of bone tissues of a femur stem on a transverse section is determined by averaging the position of the pixels of bone tissue or extrapolating the position from canal centers on inferior sections (step S21), as shown in FIG. 4A (such as the actual section shown in FIG. 13C). Superior sections may resolve bones of pelvis (ischium). If a section has resolved the ischium, an initial hole center of the femur stem is extrapolated by the calculated hole centers at inferior sections.

A vector from the center along each (total 360) integral angular position intersects the first bone boundary (step S22). The perforated boundary is elliptical, such that the distance from center 12 to the boundary changes smoothly. However, concave boundary may be caused by bone fractures or tumors, as shown in FIG. 4B. Such a concave feature 13 on the canal boundary is defined as a part of the arc from the angular position B, in which $$(r(B+1)-r(B-1))/r(B) > af \quad (1),$$

where af is a constant, r(B) is a radius (the distance from the center to the boundary) at angular position B, and r(B−1) and r(B+1) are radii of the previous and latter angular positions respectively. If $$(r(B'-1)-r(B'+1))/r(B') > af \quad (2),$$

where r(B') is a radius at the angular position B'. As the radius increases, the concave feature 13 is detected and the detection process thus terminated. "af" is generally set to 0.1 to ignore trivial spurs or fractures on hip structures. Recognition of a convex (bone spur) feature on the canal boundary resembles the concave feature recognition except that ">" (in Formula (1) and Formula (2)) is replaced by the "<".

A normal radius r(N) corresponding to each angular position inside a concave feature is interpolated using the radii (r(B) and r(B')) of both ends of the feature (as shown in FIG. 4B) (step S23). With respect to an angular position, not in a concave feature, the normal radius equals the distance from the center to the perforated boundary. Next, a cubic B-spline curve with 360 uniform parameter spacing control points is determined according to the 360 normal radii to approximate the normal boundary. Hole center 10 is reset as a center of the B-spline approximated boundary, and a radius to the outmost boundary at each integral angular position, features, normal radii, and the approximated B-spline boundary is re-determined based on the reset center.

A vector from canal center 12 along each (totally 360) integral angular position intersects all bone boundaries (as shown in FIG. 4B) (step S24). Normally, bone boundaries with the vector include the inner boundary, a boundary of the stem canal, and a stem boundary. However, more intersections may be obtained, indicating an interior hole 11 (lack of bone tissue, usually a tumor) inside the stem bone. Concave features on the outmost bone boundary caused by bone fractures or tumors are detected, determining the convex feature on the canal boundary. However, a crest or spur may form a convex feature on outmost bone boundaries, determining concave features on the canal boundary (as shown in FIG. 4B).

An axis regressed from the stem canal centers on the transverse sections is determined using a least square error method (step S25). However, if a center with a large deviation (more than 3 mm) exists, a shear displacement is identifies inside the stem. Therefore, two respective stem axes regress the two displaced parts of the stem (FIG. 4C as actual cylindrical stems in the following 3D images). A displacement under 3 mm is considered trivial and is ignored.

Figure 5:
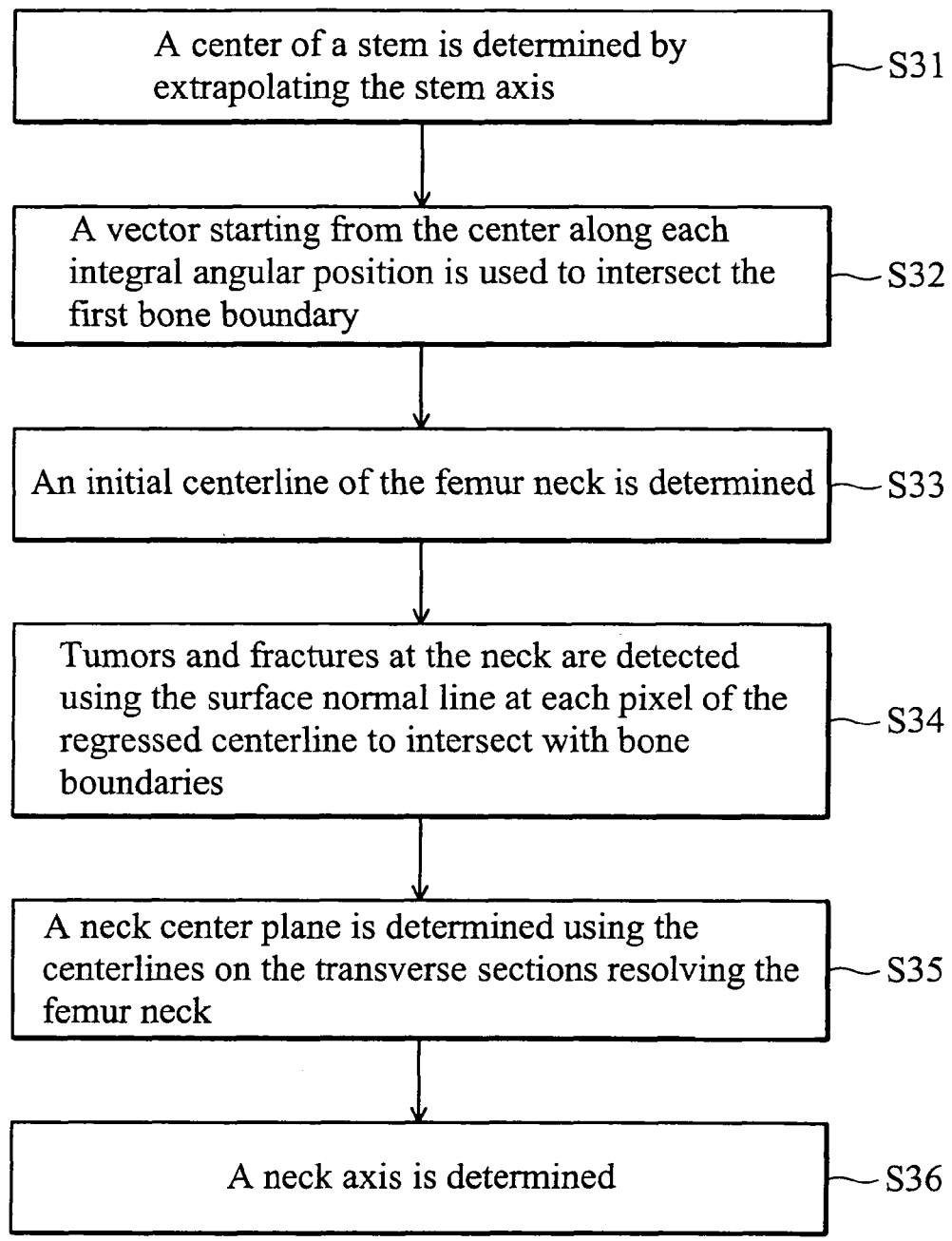
FIG. 5 is a flowchart of an embodiment of a method for excluding a femur stem and recognizing a femur neck and trochanters on transverse sections.

FIG. 5 is a flowchart of an embodiment of a method for excluding a femur stem and recognizing a femur neck and trochanters on transverse sections. In the sections, a stem canal is obscured by filling with cancerous bone A center of a stem is determined by extrapolating the stem axis (step S31), determined from previous inferior transverse sections.

Figure 6B:
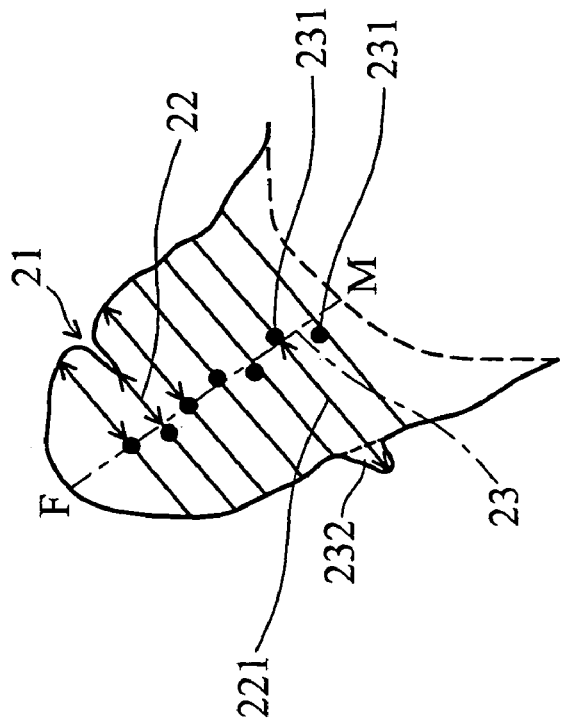
FIG. 6B is a schematic diagram of regression of neck centers for centerlines and fracture and spur feature determination.
Figure 6A:
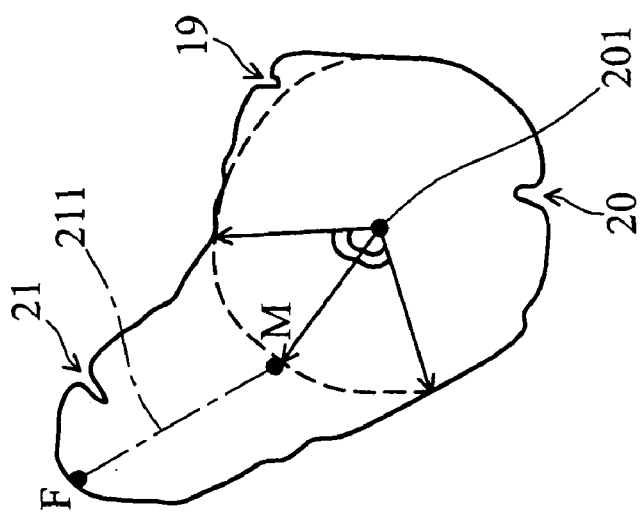
FIG. 6A is a schematic diagram of a neck and trochanter recognized as large convex features on a stem boundary and an initial centerline determined by middle points of neck feature and a farthest point to a stem center.

A vector from the center along each (totally 360) integral angular position intersects the first bone boundary (step S32). A large change in radii (from the center to the intersections) of neighboring angular positions reveals concave and convex features. Similarly, a normal radius of each angular position inside a concave or convex feature is interpolated using the radii of both ends of the feature, and the 360 normal radii to determine a cubic B-spline curve. The center of the B-spline approximated boundary is set as a center of the femur stem. Next, features and normal radii are re-determined based on the re-determined center. Small convex features are spurs, while large convex features represent the lesser and greater trochanters or femur necks located at specific angular positions, as shown in FIG. 6A. Concave features appear in the stem boundary or inside the convex trochanter.

An initial centerline (MF) of the femur neck is determined (step S33), in which M is a middle position (relating to the beginning and ending angular) of the neck feature of the stem structure, and F is point furthermost to the stem center in the neck. Along a surface normal at each pixel of the centerline, two intersections with the neck boundary and the midpoint of the two intersections are obtained, as shown in FIG. 6A. Midpoints obtained from all the pixels on the centerline can regress a new centerline (MF), as shown in FIG. 6B. Centerline endpoints MF are intersections of the centerline with the neck structure.

Tumors and fractures at the neck are detected using the surface normal line at each pixel of the regressed centerline to intersect with bone boundaries (step S34). Generally, only two intersections are obtained. Additional intersections indicate an interior hole (tumor or fracture) in the neck. A distance from the centerline to the outmost boundary normally changes smoothly. A sudden increase in the distance indicates a convex area (spurs) and decrease therein a concave area (fractures), as shown in FIG. 6B. Normal boundaries without spurs or fractures can be interpolated using neighboring normal boundaries thereof. The invention uses normal boundaries to re-determine the centerline and convex, concave, and perforated features A neck center plane is determined using the centerlines on the transverse sections resolving the femur neck (step S35). The surface normal of the neck center plane is determined by the following linear formulae, represented as:

$$A^T A W = 0 \ldots (3), \text{ where } A = \begin{bmatrix} X_1 & Y_1 & Z_1 \\ X_2 & Y_2 & Z_2 \\ X_3 & Y_3 & Z_3 \\ X_4 & Y_4 & Z_4 \end{bmatrix}, W = \begin{bmatrix} a \\ b \\ c \end{bmatrix},$$

and $(X_1, Y_1, Z_1)$, $(X_2, Y_2, Z_2)$, $(X_3, Y_3, Z_3)$, and $(X_4, Y_4, Z_4)$ are vectors of the centerlines on the sections. A position of the center plane is then regressed by the centerline endpoints on the sections. The centerline of each section is orthogonally projected onto the neck center plane to re-determine the centerline and the concave, convex, and perforated features of the neck on the section. The plane can be also extrapolate the initial centerline of neck on superior sections, in which the first step cannot be implemented to locate the initial centerline since the stem is not resolved or other areas such as the femur head appear.

Figure 6C:
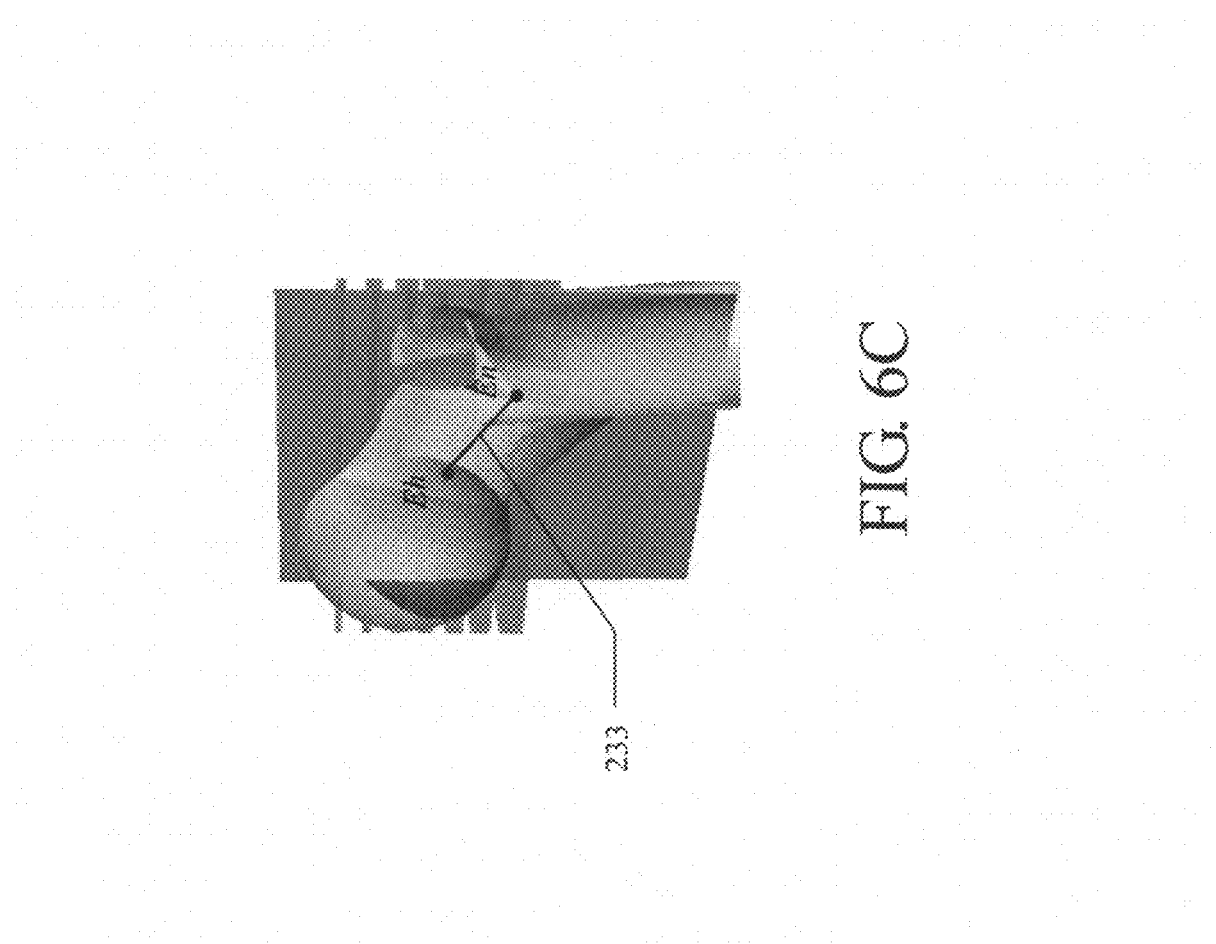
FIG. 6C is a schematic diagram of neck axis determination.

A neck axis (as EhEn shown in FIG. 6C) is determined (step S36), wherein Eh is an endpoint of the centerline on the middle section among the sections resolving the head and En is an endpoint of the centerline on the middle section among the sections resolving the neck.

Figure 7:
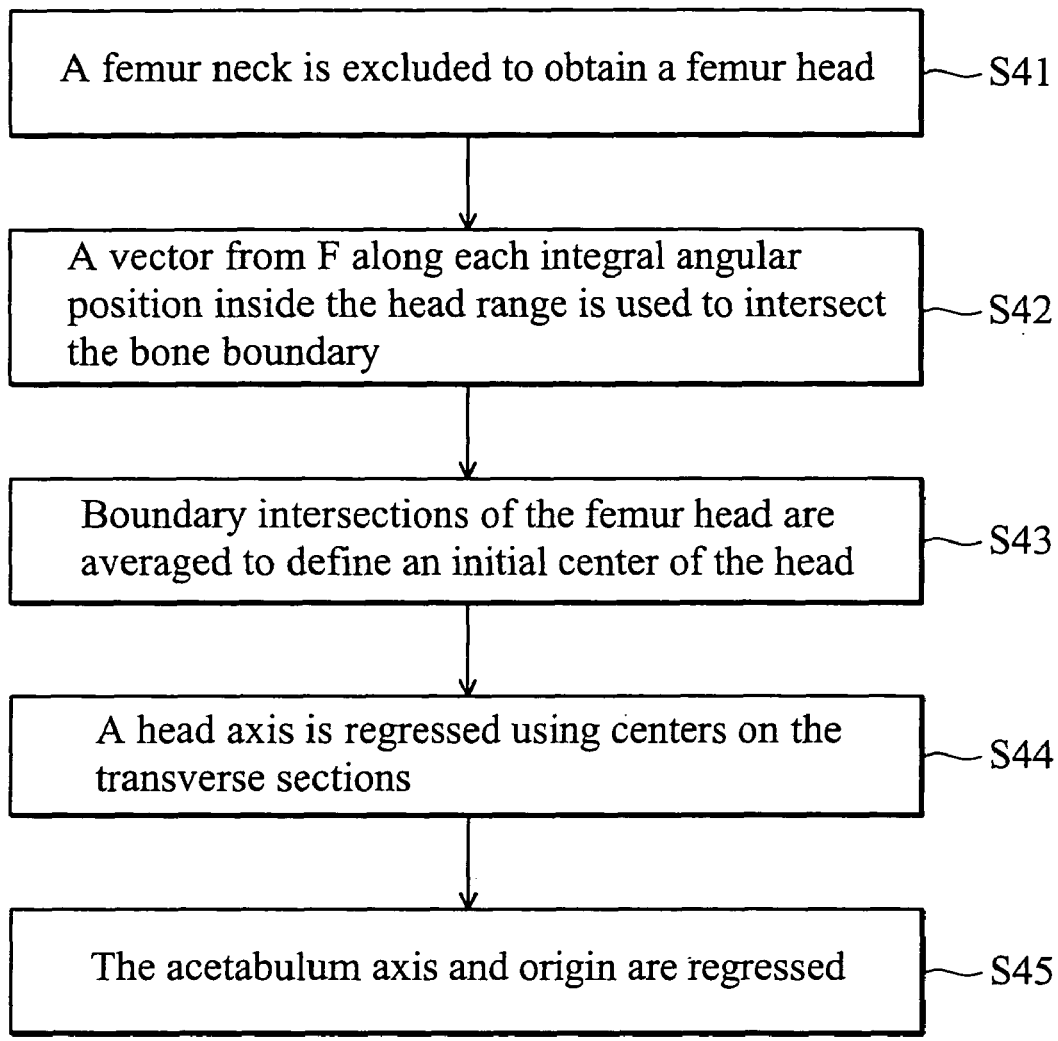
FIG. 7 is a flowchart of an embodiment of a method for femur head and acetabulum recognition.

FIG. 7 is a flowchart of an embodiment of a method for femur head and acetabulum recognition, excluding a femur neck and recognizing a femur head and acetabulum on transverse sections.

Figure 8C:
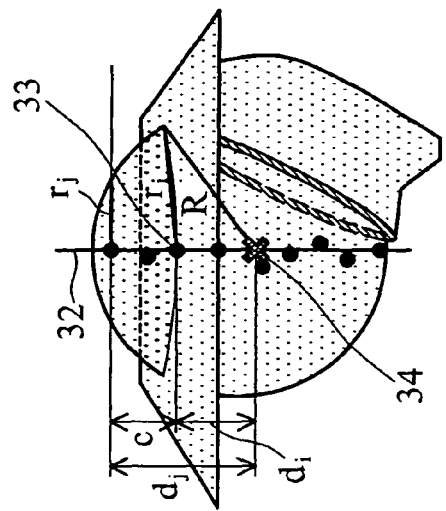
FIG. 8C is a schematic diagram of 3D head origin determination.

A femur neck is excluded to obtain a femur head (step S41). The femur head ranges between both endpoints, the two intersections of bone boundaries with the surface normal line of the centerline starting from the endpoint of the neck centerline, F as shown in FIG. 8A. If the neck is not resolved together with the head, F can be extrapolated from the endpoints of the neck centerlines on inferior sections.

A vector from F along each integral angular position inside the head range intersects the bone boundary (step S42). Multiple intersections on acetabulum and head boundaries and interior holes can also be obtained. Although a distance from F to the intersection, related to neighboring angular positions, changes smoothly, an intersection of head or acetabulum boundary can be detected according to the distance, as shown in FIG. 8A.

Figure 8B:
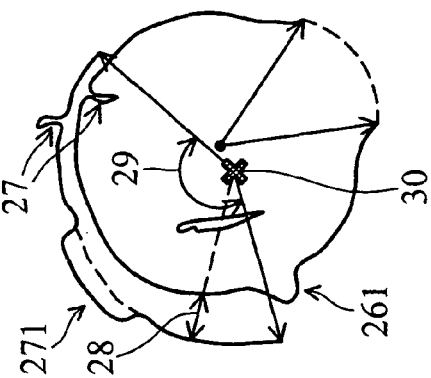
FIG. 8B is a schematic diagram of femur head and acetabulum determination using a B-spline radial boundary.
Figure 8A:
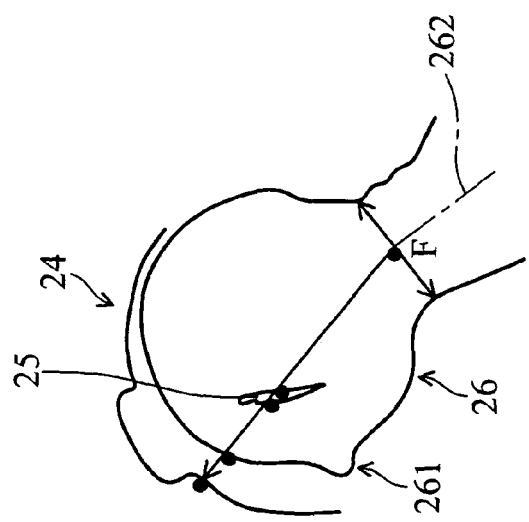
FIG. 8A is a schematic diagram of a head boundary determined according to an end of a femur neck.

Boundary intersections of the femur head are averaged to define an initial center of the head (step S43), as shown in FIG. 8B. A vector from the center along each integral angular position within the head range determines convex spurs, concave and perforated fractures, or tumors of the head and normal radii to the head boundary, as well as the convex spurs, concave fractures, and normal radii of the acetabulum using the method for femur stem recognition. The radii of the angular positions to the assumed head boundary outside the head range are the average of the normal radii inside the range. The head center and the features are re-determined according to the 360 normal radii, as well as the 360 normal radii and the average radius from the normal radii, as shown in FIG. 8B. The center, features, normal radii, and the average radius are re-determined using the described method. However, a large concave feature near the middle of the acetabulum indicates an acetabulum cave. The invention uses a vector from the head center along each integral angular position inside the head range to calculate the gap (distance) between the normal head and acetabulum boundaries (if without the concave and convex features).

A head axis 32 is regressed using centers on the transverse sections (step S44). If the transverse sections entirely cover the head, the head origin is located at the middle of the axis. If not, the following formula derived from the Pythagorean Theorem determines the head origin, represented as:

$$d_i^2 - r_i^2 = d_j^2 + r_j^2 = R^2; \; r_i^2 - r_j^2 = d_j^2 - d_i^2 = c(2d_i - c) \quad (4)$$

(as shown in FIG. 8C), where R is a 3D head radius and uniform in the head, $r_i$ and $r_j$ are 2D average radii at the i-th section and j-th sections, respectively, $d_i$ and $d_j$ are distances from the origin to the 2D center at the i-th section and j-th sections, respectively, and c is the interval between the two sections, in which $d_i$ can be solved by c and a head origin is determined by $r_i$ and $r_j$. A solution of the head origin can be obtained from the most superior section with each of the other sections resolving the head. An average of all the solutions is set as the head origin. Intersections of the head axis with the transverse sections resolve the head instead of the head centers. Then, 2D head features and gaps are re-calculated. The head origin to each pixel of the head boundary at the transversal sections determines a unit vector. The average of the vectors of all the head boundary pixels is taken as the head attitude axis.

The acetabulum axis and origin are regressed (step S45), the 2D centers, concave and convex features of the acetabulum on transverse sections are re-determined, and the acetabulum attitude vector is re-determined using the described method for the head. However, the origin can only be determined using Formula (4) as the acetabulum is not a perfectly spherical.

Figure 9:
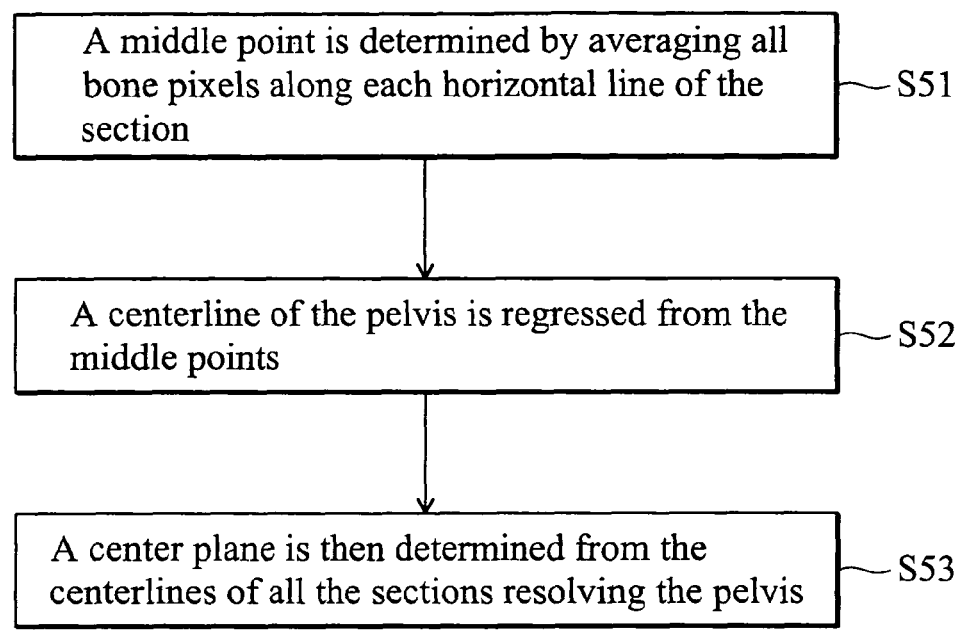
FIG. 9 is a flowchart of an embodiment of a method for recognizing a center pelvis plane on a transverse section.

FIG. 9 is a flowchart of an embodiment of a method for recognizing a pelvis center plane on a transverse section.

At a transverse section, bone areas, not parts of the femur, belong to the pelvis. The pelvis is horizontally symmetrical. Therefore, a middle point is determined by averaging all bone pixels (excluding the two femurs) along each horizontal line of the section (step S51). A centerline of the pelvis is regressed from the middle points (step S52). A center plane is then determined from the centerlines of all the sections resolving the pelvis (step S53) using the method for trochanter and femur neck recognition.

Treatments for hip diseases are categorized into conservative treatments, such as dissection and bone grafting, open reduction, hemi-arthroplasty (bipolar and single polar), and total arthroplasty. Attachments 1A~2D show the relationships between the treatments and main anatomical structures (femur stem, neck, great and lesser trochanter, head, acetabulum, and hip) with associated features (concave, convex, and interior perforated features, and radius and length deviations). Conservative treatments are applied only if there are small spurs (convex features) or fractures and benign tumors (concave and perforated features), and no angle and length (or radius) deviations in the hip structures.

Large benign tumors not generating angle and length (or radius) deviations among the hip structures are removed by dissection and bone grafting. The method of the invention obtains information relating to a position and volume of the tumor for dissection and the bone graft implantation from the feature recognition, and determines the size and origin of the bone window to dissect the tumor and graft the bone. However, if the tumor potentially results in structural instability (e.g., bone becomes too thin) during the dissection and bone grafting, plates and nails are necessary to fix the grafting bones to the dissected structure.

Open reduction uses screws or plate and nails to fix structures. Fractures in the structures result in morphological changes in bones, such as compression of a structure, and angular deviation and dislocation between two hip structures. Morphological changes must be corrected during the open reduction, comprising dislocated fractured bone fragments in hip structures, compressed femur neck and stem, trochanters and pelvis, and angular deviations inside the femur stem or between the stem and neck, the neck and head, or acetabulum and pelvis. The method of the invention calculates the positions and amounts of the morphologic changes to plan open reduction surgery.

Hemi-arthroplasty is applied in patients over 60 years of ages with large fractures on the femur neck or head or malignant tumors in the acetabulum, femur head, neck stem or trochanters. Application of bipolar or single polar hemi-prosthesis is determined based on the profession and age of the patient. Total arthroplasty is used when comminute fractures occur in the femur head or acetabulum, or Avascular Vascular Neurosis (AVN) occurs, enabling the head radius to become much smaller at the acetabulum side. The arthroplasty also reduces dislocations between the head and acetabulum to normalize the gap between the head and acetabulum.

Prosthetic components of acetabulum, and femur head, neck, and stem are determined by evaluating pathological characteristics of hip structures and associated features. Whether a pre-make or custom-made prosthesis is required depends on whether malignant tumors are present or limited in the neck and head. If a malignant tumor is inside the acetabulum, trochanter, or femur stem, a custom-made prosthesis must be used. With respect to a hemi-arthroplasty, the prosthetic head is set as the size of the head of the normal hip if the two acetabula are normal and have similar size (radius). If the two acetabula are not of similar size, the prosthetic head is determined as 0.9 times the acetabulum of the same hip. With respect to a total arthroplasty, the prosthetic acetabulum and head are selected as the size of the acetabulum and head of the normal hip. The radius of prosthetic stem refers to the largest radius of the stem canal at the subtrochanter area to meet the requirement of the proximal cortical fit. The prosthetic neck is proportional to the prosthetic head and stem. The section for insertion into the prosthetic stem refers to the stem axis and 10 mm above the lesser trochanter. However, if the stem axis has been divided into two or more, wedge shape bone grafts, plate, and nails reduce the axis deviation. Other prosthetic components of the bipolar and total prosthesis are inserted sequentially on the prosthetic stem.

Surgical procedures of the described dissection and graft, open reduction, and arthroplasty can be simulated using a reported simulator to confirm suitability of the planned surgical procedures. All sizes of template prostheses from several manufacturers are prepared before applying the described method to simulate hip arthroplasty. Prosthetic data is transferred by transferring manufacturer-provided data with standard representation into 3DS MAX software, or by interactive input into the 3DS MAX software based on real prosthetic components and manufacturer-provided cross-sections (dimensions and shapes) for each prosthesis. The prosthesis is then converted to the volume representation for implementation in a simulation system to simulate the managed modality and procedures.

The most time consuming steps are the isosurface reconstruction for 3D rendition. More than ten seconds are required for about 50 sections based on a P-IV 2.4 G with 1 Gbyte of main memory without special graphics hardware. Currently, the method divides a volume into several subvolumes and reconstructs only the isosurfaces of manipulated subvolumes, enabling the isosurface reconstruction time to take less than 1 second. Rendition of the isosurface can be less than 0.5 seconds. Change of perspective requires a rendition of the isosurface with isosurface reconstruction. With comparison of the isosurface reconstruction and rendition, computation time for feature recognition, automated diagnoses, and surgery managements are trivial.

As described, final diagnoses are confirmed by operative findings and consistent with the diagnoses obtained by the method of the invention, thus automatically diagnosing and managing hip problems based on image analyses of transverse sections. Embodiments of diagnosis and evaluation results corresponding to hip surgery, comprising acetabulum fractures, intertrochanteric fractures, femoral neck fractures, AVN of femoral heads, and tumors at intertrochanter, are shown in Attachments 1A~1D.

Two examples illustrates the image analysis method for abnormal hip structures based on transverse sections of the invention.

A process of open reduction and screw and nails for pelvis fractures follows.

Symptoms comprise severe pain with deformity over right hip and shank, suffering showed-fracture dislocation of right hip. Close reduction for the right femur head is implemented. Residual fracture for the right acetabulum with femur head displacement reveals deformity limited by movement for the right hip. As described, diagnoses comprise indicative fractures at the right acetabulum with a head displacement.

Figure 10A:
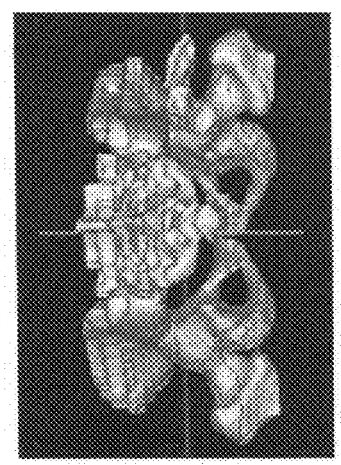
FIG. 10A is a schematic view of a 3D image rendered from the isosurface reconstructed using an MC isosurface reconstruction algorithm.
Figure 10B:
FIG. 10B is a schematic view of a transverse section resolving the acetabulum fractures.
Figure 10C:
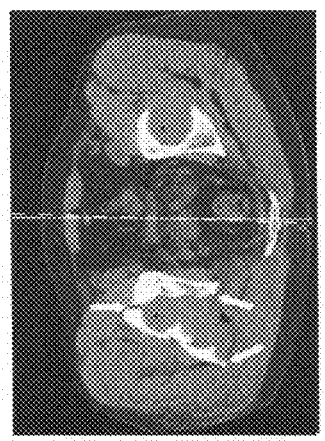
FIG. 10C is a schematic view of an image analysis result for the acetabulum on the section.

CT for the hip generates 40 transverse sections, with 3 mm intervals near the hip (acetabulum, head, neck, and trochanters) and 12 mm intervals in the superior pelvis. Linear interpolations are implemented to obtain a volume with constant (3 mm) intervals. However, the image analysis is not applied to the interpolated sections. FIG. 10A is a schematic view of a 3D image rendered from the isosurface reconstructed using an MC isosurface reconstruction algorithm. At the right hip, a femur head fracture and dislocation and fracture passing from the interface of acetabulum upward can be observed. The fractured bone segment is brought outward. FIG. 10B is a schematic view of a transverse section resolving the acetabulum fractures, also clearly demonstrating the acetabulum fractures and head dislocation. FIG. 10C is a schematic view of an image analysis result for the acetabulum on the section, from which the two femur heads are excluded for easy demonstration. The result demonstrates centers and fractures of the acetabulum, a centerline determining a pelvis center plane and intersection of the center plane with the transverse section. Deviation of the centerline from the intersection is caused due to two outward fractures at the right acetabulum.

Attachment 2 shows image analysis results of the transverse sections resolving the acetabulum fractures. In each section, two concave fractures exist on the acetabulum boundary and the centerlines determining the pelvis center plane and the standard deviation (SD) of the centerline to the center plane are demonstrated. The right gaps appear larger than the left gaps. The calculated angles between the acetabulum attitude axis of the acetabulum and the pelvis center plane are 145.06° and 140.77° for the right and left hips, respectively.

Figure 11C:
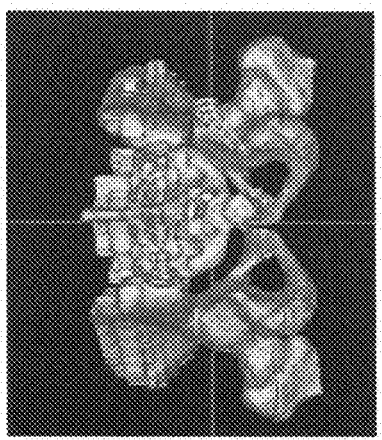
FIG. 11C is a schematic view of the calculated plate and nails and positions thereof.
Figure 11B:
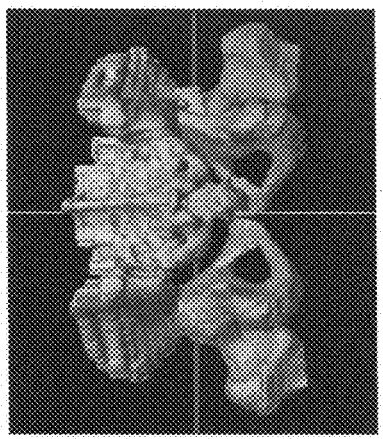
FIG. 11B is a schematic view of a cut separate fragment repositioned onto the pelvis in a translation following a 90° rotation.
Figure 11A:
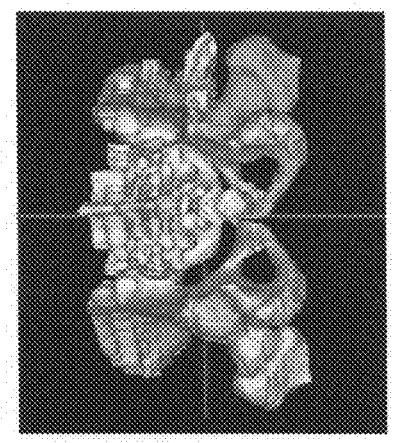
FIG. 11A is a schematic diagram of a right femur recognized and repositioned near the pelvis for dislocation reduction.

FIG. 11 shows parts of simulated images for surgery for open-reduction of pelvis fractures. FIG. 11A is a schematic diagram of a right femur recognized and repositioned near the pelvis for dislocation reduction. A swept surface of a cutting tool cuts a tuned out bone fragment. As the opposite side of the fractured fragment matches the fracture line of the pelvis, the fractured fragment is rotated to fuse the fragment with the pelvis. FIG. 11B is a schematic view of a cut separate fragment repositioned onto the pelvis in a translation following a 90° rotation. The open reduction must be practically implemented two weeks after the head reposition. Although the reduction of the fracture at the front side of the acetabulum is also implemented simultaneously, the 3D image showing this reduction is not included in this embodiment. FIG. 11C is a schematic view of the calculated plate and nails and positions thereof, fixing the repositioned fractured fragment onto the pelvis.

Hemi-arthroplasty for femur neck fracture is further illustrated.

Symptoms comprise right hip pain with limitation of motion following a fall. Abnormalities comprise external rotation of right foot, walking disability, leg discrepancy (+), and local tenderness over right inguinal area. A positive fracture line over the right femur neck is observed on X-ray, indicating right femur neck fracture.

CT for the hip generates 35 transverse sections with 3 m intervals. FIG. 13A is a schematic of a 3D image revealing a fracture on the right femur neck. FIG. 13B is a schematic of a transverse section for the right femur neck, as well as an analysis result indicating a large fracture at the right neck. FIG. 13C is a schematic of another section for the left femur neck. Regressed centerlines from the two femur necks and the fracture at the right neck are demonstrated.

Figure 14A:
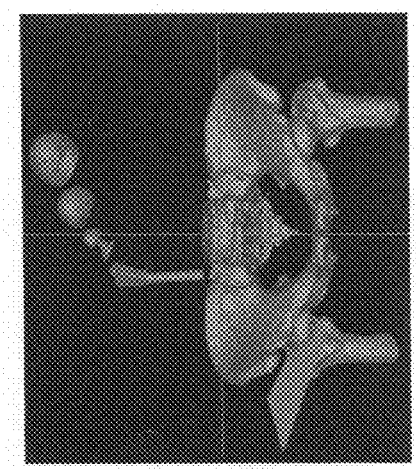
FIG. 14A is a schematic of a femur section with 5 mm above the lesser trochanter, as well as calculated optimal bipolar prosthetic stem, neck, and head.
Figure 14B:
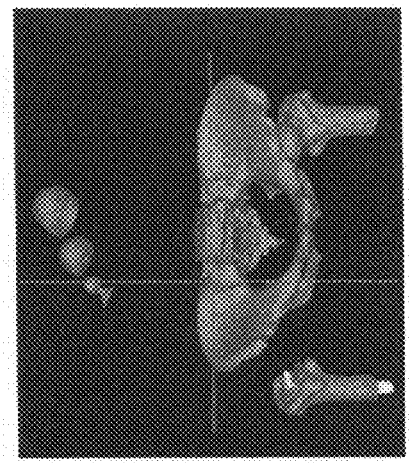
FIG. 14B is a schematic of a removed superior femur including the head, neck, and part of trochanter.
Figure 14C:
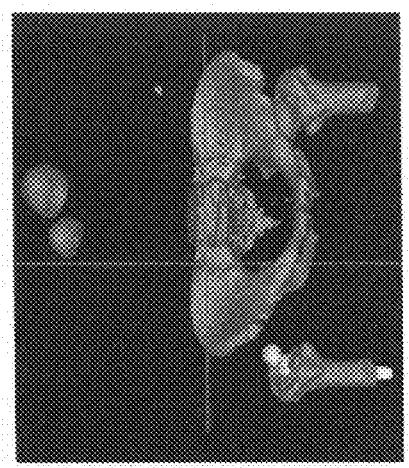
FIG. 14C is a schematic of insertion of a prosthetic neck onto the prosthetic stem.
Figure 14D:
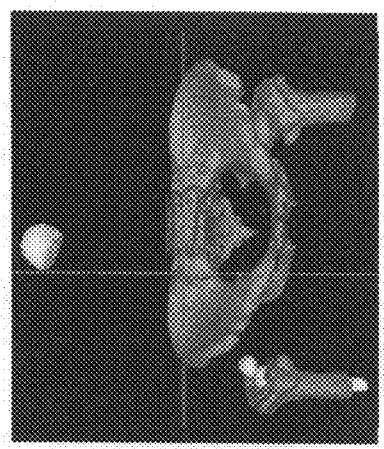
FIG. 14D is a schematic of insertion of a prosthetic inner head into the outer head.
Figure 14E:
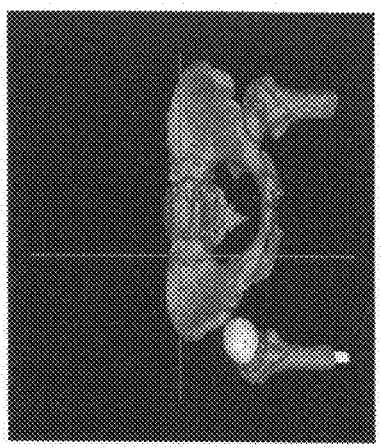
FIG. 14E is a schematic of insertion of the prosthetic head onto the prosthetic neck.
Figure 14F:
FIG. 14F is a schematic of movement of the inserted bipolar prosthesis into a desired position.
Figure 14I:
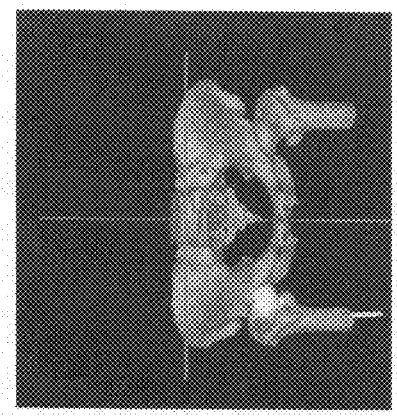
FIG. 14I is a schematic of movement of an inserted bipolar prosthesis into a desired position.
Figure 14H:
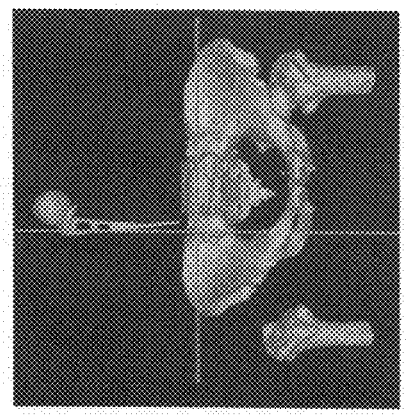
FIG. 14H is a schematic of a cut superior stem and an inserted single polar prosthesis.
Figure 14G:
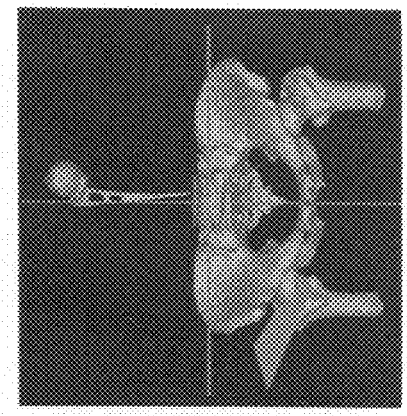
FIG. 14G is a schematic of a femur section and appearance of a calculated single polar prosthesis.

Angles between the head attitude axis and the neck axis for the right and left hips were 36.2° and 37.8° respectively, indicating a small angular deviation between the right femur neck and head. Next, hemi-arthroplasty is implemented for diagnosis. FIG. 14 shows parts of the simulation of two hemi-arthroplasty (bipolar and single polar) based on feature recognitions, evaluations, and surgical management. FIG. 14A is a schematic of a femur section with 5 mm above the lesser trochanter, as well as calculated optimal bipolar prosthetic stem, neck, and head. FIG. 14B is a schematic of a removed superior femur including the head, neck, and part of trochanter. FIG. 14B also shows recognition (highlighted as another color) and insertion of a prosthetic stem. A simulation of the invention recognizes a 3D separate structure using a closed boundary before the boundary is repositioned or deleted. FIG. 14C is a schematic of insertion (following recognition) of the prosthetic neck onto the prosthetic stem. FIG. 14D is a schematic of insertion of the prosthetic inner head into the outer head. FIG. 14E is a schematic of insertion of prosthetic head onto the prosthetic neck. FIG. 14F is a schematic of movement of the inserted bipolar prosthesis into a desired position. The position and size of the prosthesis result in good morphology matching the normal left hip and pelvis. FIG. 14G is a schematic of a femur section and appearance of a calculated single polar prosthesis. FIG. 14H is a schematic of a cut superior stem and an inserted single polar prosthesis. FIG. 14I is a schematic of movement of an inserted bipolar prosthesis into a desired position, resulting in good hip morphology. The two hemi-arthroplasty simulations indicate both the planned hemi-arthroplasty surgery achieving good hip function postoperatively.

Three-dimensional geometric estimation of pathological characteristics of hip fractures and tumors, as well as angular and distance deviations among a pelvis, acetabulum, and femur head, neck, and stem are important factors in selection of appropriate diagnostic modalities and surgical procedures for hip malady. Current techniques are mainly based on clinical experience, analyses of X-rays, observation on MRI, or CT sections without the benefits of qualitative and quantitative analyses of 3D hip morphology. The invention discloses a method for analyzing the 3D geometry of hipbones to estimate structural deviation, fractures and tumors of the hips, automatically determining precise diagnoses and surgical procedures for tumor dissection and bone graft, open reduction, and artroplasty. Another method analyzes CT transverse sections to manage a prosthetic stem.

The invention uses radial B-spline curves to approximate a stem canal, femur head and, acetabulum as elliptical structures, and a least square method to approximate a femur neck as trapezoidal and pelvis as horizontally symmetrical structures at each transverse section. Concave, convex, or perforated features on the described structures are recognized as fractures, tumors, or spurs. Centers of the elliptical structures obtained from the transverse sections determine 3D structural axes, and centerlines of the cone-like and symmetrical structures determine 3D structural center planes. The invention evaluates dislocations and angular deviations among the structures and detects structural deformities, comprising head radius compression using structural properties, and thus determines parameters, comprising distances and angles, in hip surgery to reposition the structures for reduction of the dislocations and angular deviations.

Unlike 2D transverse sections, 3D reconstructed isosurfaces by volume visualization techniques result in unclear anatomical features and thus cannot provide significant diagnostic information. Unlike the 3D reconstruction approach, the method of the invention analyzes anatomical features in 2D sections and integrates these 2D features to obtain 3D structures with associated features, and then structure and feature properties. Since simple 3D geometric entities, such as lines and planes, evaluate the structural properties, estimations using these entities (e.g. the angle between the femur stem and neck axes) are close to general values, indicating evaluation based on the 3D entities of hip structures are acceptable.

The invention combines diagnostic and management tools with surgical simulation tools for automated diagnosis, surgical planning and verification, prognosis assessment and management, thus providing not only accurate diagnosis but also detailed surgical parameters, comprising angles and distances for reduction, sizes of prosthetic components, and position and volume for sectioning, opening and dissecting, and grafting. The invention avoids the need for trial-and-error based of fitting of template prostheses and use of various guide tools, saving surgical time.

Although the present invention has been described in terms of preferred embodiment, it is not intended to limit the invention thereto. Those skilled in the technology can still make various alterations and modifications without departing from the scope and spirit of this invention. Therefore, the scope of the present invention shall be defined and protected by the following claims and their equivalents.

What is claimed is:

1. An image analysis method for abnormal hip structures, comprising:
   providing a plurality of transverse sections of a bone structure;
   recognizing at least one hip structure from the transverse sections, wherein the hip structure comprise a femur neck, and the recognition of the hip structure comprises the steps of:
   determining a center of a femur stem by extrapolating a femur stem axis;
   intersecting a first bone boundary using a vector from the initial center along each integral angular position;
   interpolating a normal radius inside a concave or convex feature using radii of both ends of the structural feature;
   determining an initial centerline of the femur neck;
   regressing a new centerline according to midpoints from each pixel on the initial centerline;
   detecting tumors and fractures at the femur neck using surface normal lines at each pixel of the regressed centerline;
   determining a center plane of the femur neck according to the centerlines on the transverse sections resolving the femur neck;
   orthogonally projecting the centerlines of each transverse sections onto the center plane of the femur neck to re-determine a centerline of the transverse sections and structural features of the femur neck; and
   determining a femur neck axis according to the re-determined centerline and structural features;
   recognizing abnormities of the hip structure by respectively recognizing concave, convex, and perforated features on the hip structure as fractures, tumors, and spurs, and calculating structural and feature properties for the abnormities of the hip structure; and
   determining whether the hip structure is abnormal or not, or determining a restoration operation for the hip structure according to the calculated structural and feature properties of the hip structure.

2. The method as claimed in claim 1, wherein bone structure recognition further comprises:
   determining an initial center of each stem canal on the transverse sections by averaging pixel positions of the bone structure or extrapolating the positions according to stem canal centers on inferior sections;
   intersecting a first bone boundary using a vector from the initial center along each integral angular position;
   interpolating a normal radius corresponding to each angular position inside a concave feature using radii of both ends of the concave feature of the stem canal;
   intersecting all bone boundaries using a vector from the stem canal centers along each integral angular position; and
   determining an axis regressed from the stem canal centers on the transverse sections.

3. The method as claimed in claim 2, wherein normal radius interpolation further comprises:
   determining a cubic B-spline curve according to the normal radius to approximate the normal boundary of the stem canal;
   resetting a hole center as a center of a B-spline approximated boundary; and
   re-determining a radius to an outmost boundary at each integral angular position, features, normal radii, and the approximated B-spline boundary based on the reset center.

4. The method as claimed in claim 2, wherein boundary intersection further comprises detection concave features of the outmost boundary of stem canal.

5. The method as claimed in claim 1, wherein normal radius interpolation further comprises:
   determination of a cubic B-spline curve according to a normal radius of the femur stem axis to approximate a normal boundary of the stem canal;
   setting a center of a B-spline approximated boundary as a center of the femur stem; and
   re-determination of the structural features and normal radius based on the re-determined center.

6. The method as claimed in claim 1, wherein bone structure recognition further comprises:
   excluding a femur neck to obtain a femur head;
   intersecting boundaries of femur head using a vector from an outmost point along each integral angular position to obtain multiple boundary intersections;
   averaging the boundary intersections to define an initial center of the head;
   determining structural features and normal radii to the boundaries of the femur head and the acetabulum using a vector from the initial center along each integral angular position;
   re-determining a center of the femur head and structural features according to the normal radii of the femur head; and
   regressing an axis of the femur head using centers on the transverse sections.

7. The method as claimed in claim 6, further comprising regressing an axis and origin of the acetabulum and re-determining 2D centers and concave and convex features of the acetabulum on the transverse sections to re-determine attitude vectors of the acetabulum accordingly.

8. The method as claimed in claim 6, wherein the axis of the femur head is regressed using Pythagoras theorem.

9. The method as claimed in claim 1, wherein bone structure recognition further comprises:
   determining a middle point of the pelvis by averaging bone pixels thereof along each horizontal line of the transverse sections;
   regressing centerlines of the pelvis from the middle points; and
   determining a center plane according to the centerlines of the transverse sections.

10. The method as claimed in claim 1, further comprising recognizing the concave, convex and, perforated features as fractures, tumors, and spurs.

11. The method as claimed in claim 1, wherein abnormalities relating to the bone structures comprise deviated angles and dislocations between the hip structure and tumor.

12. The method as claimed in claim 1, wherein the transverse sections are generated using CT or MRI.

13. The method as claimed in claim 1, further comprising approximating a stem canal, femur head, or acetabulum on the transverse sections as elliptical structures using a B-spline function, or a femur neck as cylindrical structures and a pelvis horizontally as symmetrical structures using a least square method.

* * * * *